United States Patent
Short (10) Patent No.: US 6,232,103 B1
(45) Date of Patent: May 15, 2001

(54) METHODS USEFUL FOR NUCLEIC ACID SEQUENCING USING MODIFIED NUCLEOTIDES COMPRISING PHENYLBORONIC ACID

(75) Inventor: Jay M. Short, Encinitas, CA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/274,711

(22) Filed: Mar. 23, 1999

Related U.S. Application Data (60) Provisional application No. 60/078,969, filed on Mar. 23, 1998.

(51) Int. Cl.[7] ................................................. C12P 19/34
(52) U.S. Cl. ........................................ 435/91.1; 435/91.2
(58) Field of Search ................................... 435/91.1, 91.2

(56) References Cited

U.S. PATENT DOCUMENTS

| | | | |
|---|---|---|---|
| 5,151,507 | * | 9/1992 | Hobbs, Jr. et al. ............... 536/23 |
| 5,597,909 | * | 1/1997 | Urdea et al. ...................... 536/24.3 |
| 5,831,045 | * | 11/1998 | Stolowitz et al. ............... 536/22.1 |
| 5,831,046 | * | 11/1998 | Stolowitz et al. ............... 536/22.1 |
| 5,852,178 | * | 12/1998 | Stolowitz ........................ 530/402 |
| 5,876,938 | * | 3/1999 | Stolowitz et al. ................. 435/6 |
| 6,013,783 | * | 11/1998 | Kaiser et al. .................... 536/23.1 |

FOREIGN PATENT DOCUMENTS

| | | | |
|---|---|---|---|
| 0157280A2 | 10/1985 | (EP) | ............... G01N/27/26 |
| WO95/20591A | 8/1995 | (WO) | ............... C07F/5/02 |
| WO97/27331 | 7/1997 | (WO) | ............... C12Q/1/68 |
| WO98/16661 | 4/1998 | (WO) | ............... C12Q/1/68 |

OTHER PUBLICATIONS

C. Duplaa et al., Quantitative Analysis of Polymerase Chain Reaction Products Using Biotinylated dUTP Incorporation, Anal. Biochem., vol. 212, pp. 229–236, 1993.

\* cited by examiner

*Primary Examiner*—Kenneth R. Horlick
(74) *Attorney, Agent, or Firm*—Gray Cary Ware & Freidenrich LLP; Lisa A. Haile (57) ABSTRACT

The present invention relates to a method for sequencing nucleic acids. In particular, such method includes incorporating certain modified nucleotides referred to as Simtides into nucleic acid strands. These Simtides are complexes comprising a nucleotide base (or analog thereof), a linker, and a label capable of generating a detectable signal for sequencing. A Simtide may be incorporated into a sequencing fragment as a primer component, as a chain elongator, or as a chain terminator.

9 Claims, 3 Drawing Sheets

METHODS USEFUL FOR NUCLEIC ACID SEQUENCING USING MODIFIED NUCLEOTIDES COMPRISING PHENYLBORONIC ACID

This application claims the benefit of U.S. Provisional Application Ser. No. 60/078,969 filed Mar. 23, 1998.

BACKGROUND OF THE INVENTION

The present invention relates generally to a method for obtaining nucleic acid sequence information. More specifically, the present invention provides certain modified nucleotides referred to as Simtides for use in nucleic acid sequencing reactions.

Nucleic acid sequencing is a critical analytical technique used in the field of molecular biology. The development of reliable methods for sequencing has led to great advances in the understanding of the organization of genetic information and has laid the foundation for the detailed analysis of the structure and function of genes. Several methods have been developed to determine the nucleotide sequence of nucleic acids.

Two general methods currently used to sequence DNA include the Maxam-Gilbert chemical degradation method (A. M. Maxam et al., *Methods in Enzymology* 65, 499–559 (1980)) and the Sanger dideoxy chain termination method (F. Sanger, et al., *Proc. Natl. Acad. Sci. USA* 74, 5463–5467 (1977)). Both of these techniques are detailed in *Molecular Cloning: A Laboratory Manual* (Sambrook, Fritsch, Maniatis, eds., Cold Spring Harbor Laboratory Press, 1989), the disclosure of which is incorporated herein by reference.

With the Maxam-Gilbert technique, DNA fragments are prepared through base-specific chemical cleavage of the piece of DNA to be sequenced. The piece of DNA to be sequenced is first 5'-end-labeled with $^{32}P$ and then divided into four portions. Each portion is subjected to a different set of chemical treatments designed to cleave DNA at positions adjacent to a given base (or bases). The result is that all labeled figments will have the same 5'-terminus as the original piece of DNA and will have 3'-termini defined by the positions of cleavage. This treatment is performed under conditions that generate DNA figments of convenient lengths for separation by gel electrophoresis.

With the Sanger technique, DNA fragments are produced through partial enzymatic copying (i.e., synthesis) of the piece of DNA to be sequenced. In the most common version, the piece of DNA to be sequenced is inserted, using standard techniques, into a "sequencing vector", a large circular, single-stranded piece of DNA such as the bacteriophage M13. This becomes the template for the copying process. A short piece of DNA with a sequence complementary to a region of the template just upstream from the insert is annealed to the template to serve as a primer for the synthesis. In the presence of the four natural deoxyribonucleoside triphosphates (dNTP's), a DNA polymerase will extend the primer from the 3'-end to produce a complementary copy of the template in the region of the insert. To produce a complete set of sequencing fragments, four reactions are run in parallel, each containing the four dNTP's along with a single dideoxyribonucleoside triphosphate (ddNTP) terminator, one for each base. $^{32}P$-labeled or fluorophore-labeled dNTP is added to afford labeled fragments. If a dNTP is incorporated by the polymerase, chain extension can continue. If the corresponding ddNTP is selected, the chain is terminated. The ratio of ddNTP to dNTP is adjusted to generate DNA fragments of appropriate lengths. Each of the four reaction mixtures will, thus, contain a distribution of fragments with the same dideoxynucleoside residue at the 3'-terminus and a primer-defined 5'terminus.

Fragments generated utilizing the Sanger method of sequencing may be end-labeled, via, for example, the utilization of primers having labeled nucleotides incorporated into their sequence. Alternatively, molecules may be end-labeled via the utilization of labeled dideoxynucleosides or other modified chain-terminating nucleotides or nucleotide mimics. Molecules can also be labeled internally by the utilization of one or more labeled nucleotides incorporated during the synthesis step of the process.

In both the Sanger and Maxam-Gilbert methods, base sequence information, which generally cannot be directly determined by physical methods, is converted into chain-length information, which can be determined. This determination can be accomplished through electophoretic separation. Under denaturing conditions (e.g., high temperature, presence of urea, etc.), short DNA fragments migrate as if they were stiff rods. If a gel matrix is employed for the electrophoresis, the DNA fragments are sorted by size. The single-base resolution required for sequencing can usually be obtained for DNA fragments containing up to several hundred bases. To determine a full sequence, the four sets of figments produced by either Maxam-Gilbert or Sanger methodology are subjected to electrophoresis. This results in the fragments being spatially resolved along the length of the gel.

Dyes such as, for example, infrared dyes, fluorescent dyes, colorimetric dyes, chemiluminescent dyes, and/or other detectable molecules, can be used instead of the $^{32}P$ label in the foregoing sequencing reactions. Molecules other than dideoxynucleotides may also be used as chain terminators in these reactions.

One method of discriminating dyes in these types of reactions is described in U.S. patent application Ser. No. 07/057,566 (Prober et al.) filed Jun. 12, 1987, abandoned, entitled "Method, System, and Reagents for DNA Sequencing". This system is available from E. I. Du Pont de Nemours and Company (Wilmington, Del.), and is known as the Genesis™ 2000. The system comprises a means for detecting the presence of radiant energy from closely-related yet distinguishable reporters or labels that are covalently attached to compounds which function as chain-terminating nucleotides in a modified Sanger DNA chain-elongation method. Distinguishable fluorescent reporters are attached to each of the four dideoxynucleotide bases represented in Sanger DNA-sequencing reactions, i.e., dideoxynucleotides of adenine (A), guanine (G), cytosine (C), and thymine (I). These reporter-labeled chain-terminating reagents are substituted for unlabeled chain terminators in the traditional Sanger method and are combined in reactions with the corresponding deoxynucleotides, an appropriate primer, template, and polymerase. The resulting mixture contains DNA fragments of varying length that differ from each other by one base and terminate on the 3'-end with uniquely labeled chain terminators corresponding to one of the four DNA bases. This labeling method allows elimination of the customary radioactive label contained in one of the deoxynucleotides of the traditional Sanger method.

Detection of these reporter labels can be accomplished with two stationary photomultiplier tubes (PMT's) that receive differing wavelength bands of fluorescent emissions from laser-stimulated reporters attached to chain terminators on the DNA fragments. These fragments can be electrophoretically separated in space and/or time to move along an axis perpendicular to the sensing area of the PMT's. The fluorescent emissions first pass through a dichroic or other wavelength-selective filter or filters, placed so as to direct one characteristic wavelength to one PMT and the other characteristic wavelength to the other PMT. In this manner, different digital signals are created in each PMT that can be ratioed to produce a third signal that is unique to a given fluorescent reporter, even if a series of fluorescent reporters have closely-spaced emission wavelengths. This system is capable of detecting reporters with efficiently-spaced emissions whose-maxima differ by only 5 to 7 nm. Therefore, the sequential base assignments in a DNA strand of interest can be made on the basis of the unique ratio derived for each of the four reporter-labeled chain terminators which correspond to each of the four bases in DNA.

Although the base information in the Genesis™ system is contained in fluorescent labels, the information may also be contained in colorimetric labels (S. Beck, *Anal. Biochem.* 164(2), 514–520 (1987)), chemiluminescent labels (S. Beck, *Nucleic Acids Research* 17, 5115–5123 (1989)), or other labels.

The Genesis™ DNA sequencer is designed to take advantage of the dideoxy chain termination chemistry. In order to employ this chemistry, it is necessary to use four chemically-similar dyes to distinguish the four bases, A, C, G, and T. Unless the dyes are carefully chosen and exhaustively evaluated, their electrophoretic mobility may differ in some DNA sequences, leading to a scrambling of sequence information. The four dyes, chosen for similar electrophoretic mobility, have overlapping emission and excitation spectra. The need to distinguish these dyes without the excessive light loss of extremely narrow-band filters led to a two-channel detection scheme in which the ratio of two signals is used to determine which base has passed the detector. When peaks are well-resolved and noise-free, the ratiometric signals are easy to interpret However, to maximize the amount of sequence information that can be obtained from each run, it is necessary to accurately interpret the two-channel signal under conditions of poor peak resolution and significant noise.

Sequencers employing primer chemistry have also been described (L. M. Smith, et al., *Nucleic Acids Research* 13, 2399–2412 (1985), and W. Ansorge, et al., *J. Biochem Biophys. Meth.* 13, 315–323 (1986)). These sequencers employ four channels, one for each base. Other sequencers, such as that described by Kambara, et al., *Biotechnology* 6, 816–821 (1988), employ one signal in each of four electrophoresis lanes. These systems employ yet another class of data analysis methods, since the results from four separate lanes must be registered or aligned in the proper time sequence.

Sequencers employing primer chemistry, such as Hunkapiller, et al., U.S. Pat. No. 4,811,218, are not so restricted in the selection of dyes that may be used to tag the DNA fragments. These sequencers can employ four signal channels (one for each base) and, thus, do not require the complex algorithms needed to interpret ratiometric signals. On the other hand, these sequencers do not enjoy the advantages of terminator chemistry. In particular, primer chemistry requires four separate reaction tubes for each sample to be sequenced, while terminator chemistry requires only one.

The present invention is applicable to any sequencing strategies employing the Sanger or Maxam-Gilbert methods, or modifications thereof. The present invention is also applicable to any sequencing strategy where a label is associated with a nucleotide or nucleic acid. Examples of such sequencing strategies are described in U.S. Pat. No. 5,667,972, entitled "Method of Sequencing of Genomes by Hybridization of Oligonucleotide Probes", and in U.S. Pat. No. 5,652,103, entitled "Method for Sequencing Synthetic Oligonucleotides Containing Non-Phosphodiester Internucleotide Linkages".

Modified nucleotides carrying a detectable moiety (i.e., reporter), either radioisotopic or non-radioisotopic, have been useful in nucleic probes and oligonucleotide labeling. Nucleic acid probes containing a modified nucleotide that has a reporter group attached via a linker arm to a base have been reported. For example, Langer, et al., *Proc. Natl. Acad Sci. USA* 78(11), 6633–6637 (1981), describes the attachment of biotin to the C-5 position of dUTP by an allylamine linker arm. The attachment of biotin and other reporter groups to the 5-position of pyrimidines via a linker arm is also discussed in U.S. Pat. No. 4,711,955. Nucleotides labeled via a linker arm attached to the 5- or other positions of pyrimidines are also suggested in U.S. Pat. No. 4,948,882.

Bisulfite-catalyzed transamination of the N4-position of cytosine with bifunctional amines is described by Schulman, et al., *Nucleic Acids Research* 9(5), 1203–1217 (1981) and Draper, et al., *Biochemistry* 19, 1774–1781 (1980). By this method, fluorescent labels are attached via linker arms to cytidine or cytidine-containing polynucleotides. The attachment of biotin to the N4-position of cytidine is disclosed in U.S. Pat. No. 4,828,979, and the linking of detectable moieties to cytidine at the N4-position is also set forth in U.S. Pat. Nos. 5,013,831 and 5,241,060.

U.S. Pat. No 5,407,801 describes the preparation of an oligonucleotide triplex wherein a linker arm is conjugated to deoxycytidine via bisulfite-catalyzed transamination. The linker arms disclosed therein include an aminoalkyl or carboxyalkyl linker arm.

U.S. Pat. No. 5,405,950 describes cytidine analogs in which a linker arm is attached to the N4-position of the cytosine base. The linker arm is terminated with a protecting group, which prevents the penultimate residue of the linker arm from reacting with the N-hydroxysuccinimide ester of biotin amino caproic acid.

Historically, several essential criteria had to be satisfied in order for a modified nucleotide to be generally suitable as a substitute for a labeled form of a naturally occurring nucleotide. First, the modified compound had to contain a substituent that was unique, i.e., not normally associated with nucleotides or polynucleotides. Second, the molecules had to react specifically with chemical or biological reagents to provide a sensitive detection system. Third, the analogs had to be relatively efficient substrates for commonly studied nucleic acid enzymes, since numerous practical applications require that the analog be enzymatically metabolized (e.g., the analogs themselves had to function as substrates for nucleic acid polymerases). Accordingly, ring structures of bases were not modified at positions that sterically, or in any other way, interfered with the normal Watson-Crick hydrogen bonding potential of the bases. Otherwise, the substituents would yield compounds that were inactive as polymerase substrates. Substitution at ring positions that altered the normal "anti" nucleoside conformation had to be avoided, since such conformational changes usually render nucleotide derivatives unacceptable as polymerase substrates. Normally, such considerations limit substitution positions to the 5-position of a pyrimidine and the 7-position of a purine or a 7-deazapurine. Fourth, the detection system required the ability to interact with substituents incorporated into polynucleotides so as to be compatible with nucleic acid hybridization methodologies. Thus, it was preferable that detectable moieties be attached to the purine or pyrimidine through a chemical linkage or "linker arm" so that it could readily interact with antibodies, other detector proteins, or chemical reagents.

For reactions requiring hybridization steps, such as the sequencing strategy discussed in U.S. Pat. No. 5,667,972 described above, linkages that attach detectable molecules to nucleotides have had to withstand all experimental conditions to which normal nucleotides and polynucleotides are routinely subjected (e.g., extended hybridization times at elevated temperatures, phenol and organic solvent extraction, electrophoresis, etc.).

While the art has made significant strides, there still exists a need for modified nucleotides which have the ability to replace one or more natural nucleotides and which facilitate labeling of single or double stranded DNA or RNA for use in sequencing reactions. For example, labeled dideoxynucleotides have historically been more difficult than natural nucleotides to incorporate efficiently into growing nucleic acid chains in sequencing reactions. The method of the present invention addresses this need.

The method of the present invention permits detectable molecules to be associated with nucleic acids before, during, or subsequent to sequencing reactions to facilitate labeling and detection. All types of labels (i.e., detectable molecules) may be utilized in the practice of the present invention, including but not limited to infrared, fluorescent and colorimetric labels. In the present invention, multiple reactions can be performed in each sequencing lane and any nucleic acid polymerase may be used. A single reaction condition can be utilized for all types of labels, particularly where labels are associated with linker molecules subsequent to incorporation. Furthermore, sequencing can be performed utilizing chain termination or primer labeling techniques.

SUMMARY OF THE INVENTION

It is an object of the present invention to provide a modified nucleotide (Simtide) for use in nucleic acid sequencing reactions. These Simtides are also useful in any other reaction requiring a labeled nucleotide, including labeling and probing reactions. Another object of the present invention is a method for obtaining nucleic acid sequence information using said Simtides.

DETAILED DESCRIPTION OF THE INVENTION

The present invention provides a molecule referred to as a Simtide that certain modifying enzymes, in particular nucleic acid polymerases, can incorporate without bias into growing nucleic acid strands, while permitting the use of any desired detectable labeling molecule to facilitate detection of fragments in a sequencing reaction. In accordance with the present invention, Simtides are utilized in recombinant DNA techniques requiring detection of a nucleotide or polynucleotide.

In standard dideoxy sequencing reactions, template nucleic acid molecules are incubated in four separate reactions with primers, nucleotides (all four), and dideoxy (chain terminator) nucleotides (different dideoxy nucleotide for each reaction). Aver primer hybridization, polymerase is added to the mixture and extension proceeds. The incorporation of a dideoxy nucleotide terminates the extension reaction. The presence in a reaction of both regular nucleotide and the terminator version of a nucleotide ensures that the termination will not occur every time the nucleotide is required to be incorporated. Thus, this random incorporation of dideoxy nucleotides yields fragments, which can be distinguished based on size when denatured and separated by electrophoresis.

Primers (oligonucleotides) used in sequencing reactions can be chemically synthesized such that synthetic strands of nucleic acid are rapidly and effectively produced. A widely utilized chemical procedure for the synthesis of oligonucleotides is referred to as the phosphoramidite methodology. See, e.g., U.S. Pat. No. 4,414,732; McBride, L. and Caruthers, M., Tetrahedron Letters, 24, 245–248 (1983); and Sinha, N. et al., Nucleic Acids Research 17, 4539–4557 (1984), the disclosures of which are incorporated herein by reference. Commercially available oligonucleotide synthesizers based upon the phosphoramidite methodology include, for example, the Biosearch 8750™ and ABI 380B™, 392™ and 394™ DNA synthesizers.

Fragments generated by the above method are labeled for detection by a variety of methods. Radioactive, fluorescent or infrared dye labels may be employed. Primers are labeled, or chain-terminating molecules (for example, dideoxy nucleotides) are labeled. One problem encountered with labeling chain terminator molecules is that polymerases do not generally incorporate each terminator molecule with equal efficiency. Nucleotides or nucleosides associated with linker molecules in accordance with the methods of the present invention can be utilized in sequencing reactions to overcome this problem. Polymerases can incorporate nucleotides associated with linker moieties with equal efficiency. Labels can then be associated with sequencing fragments subsequent to the sequencing reaction to effectively yield a complete incorporated Simtide, and the process of detection can be completed.

A Simtide, as used herein, is a complex comprising three components: a nucleic acid base (or analog thereof), a linker, and a "detector" molecule or label that can, either by itself or by reacting or associating with another molecule generate a detectable signal. Complete or partial Simtides can be incorporated into sequencing fragments in a variety of places (e.g., in the primers, in elongating chain fragments, or as chain terminators in sequencing reactions).

Primers can be generated synthetically using techniques well known in the art utilizing naturally occurring nucleotides, novel or unique nucleotides, or nucleotide analogs. Complete, or more preferably, partial Simtides, can be incorporated into the primers during their synthesis. Partial Simtides are nucleotides, novel or unique nucleotides or nucleotide analogs associated with complete or partial linker molecules. Partial linker molecules are molecules that can associate to generate a complete linker molecule. If partial linker molecules are associated with nucleotides during primer synthesis, complete Simtides can be generated upon association of the nucleotide/partial linker molecule with a partial linker/detectable molecule before, during or after the sequencing reaction. Alternatively, if complete linker molecules are associated with nucleotides during primer synthesis, complete Simtides can be generated upon association with detectable molecules before, during or after the sequencing reaction.

Complete or partial Simtides can also be incorporated into sequencing fragments in elongating chain fragments. Nucleotides, novel or unique nucleotides, or nucleotide analogs associated with partial or complete linkers, can be synthesized and utilized as replacements for one or more of the nucleotide components of sequencing reactions added to the reaction to allow elongation and synthesis of new fragments. Detectable molecules can be added before, during, or after the sequencing reaction to yield complete Simtides if partial linkers are utilized.

Figure 3:
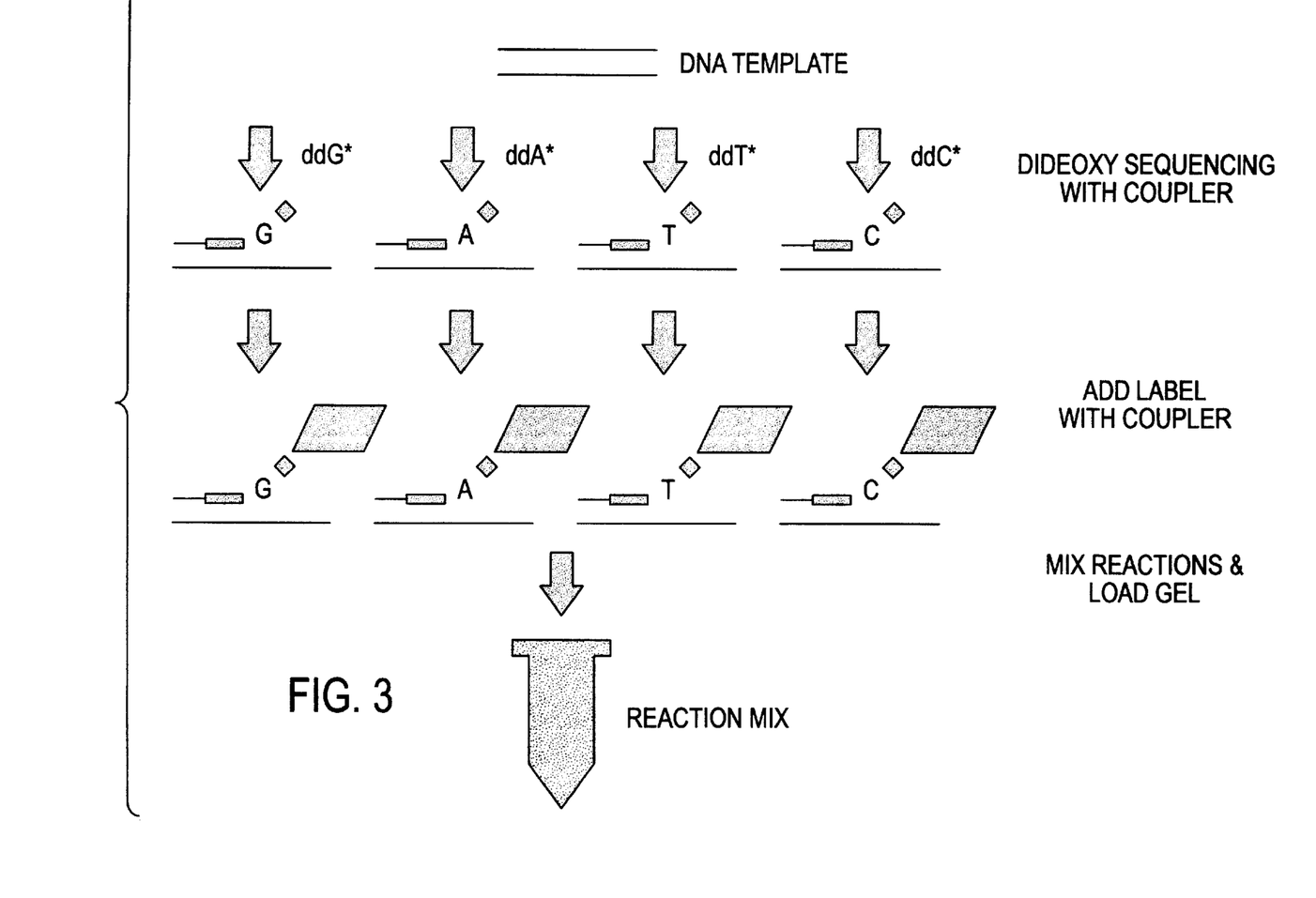
FIG. 3 depicts how nucleic acid templates (DNA in this depiction) may be sequenced utilizing dideoxynucleotides associated with components of linker molecules. Labels (detectable molecules) associated with other components of linker molecules are then added to modified nucleic acids to yield labeled molecules. Reaction mixtures are electrophoresed on sequencing gels to complete the sequencing process.

Complete or partial Simfides can also be incorporated into sequencing fragments as chain terminators. Dideoxynucleotides, novel or unique dideoxynucleotides, or dideoxynucleotide analogs associated with partial or complete linkers can be synthesized and utilized as chain terminator components of sequencing reactions. Detectable molecules can be added before, during, or after the sequencing reaction to yield complete Simtides if partial linkers are utilized. FIG. 3 depicts this aspect of the present invention.

Association to linkers or linker components can also occur prior to or after primer or sequencing fragment generation. Thus, Simtides can be incorporated as a complete complex or portions thereof may be incorporated prior to a reaction and complete complexes generated thereafter. For example, a base associated with a linker component may be incorporated into a primer, during elongation of a sequencing fragment, or as a chain terminator in the sequencing reaction, followed by a reaction to generate a complete complex by associating a detector molecule (also associated with a linker component) to the fragment. Alternatively, linkers associated with detector molecules can be associated with sequencing fragments after the sequencing reaction is complete.

Accordingly, one aspect of the present invention provides a Simtide useful in sequencing, labeling or probing reactions having the structure:

wherein X is a nucleotide base, base analog, or any other base mimic which may be incorporated by a nucleic acid polymerase in a polymerization reaction, PBA is a reversible linker, and Y is a detectable molecule.

Another aspect of the present invention provides a Simtide useful in sequencing, labeling or probing reactions having the structure:

wherein X is a nucleotide base, base analog, or any other base mimic which may be incorporated by a nucleic acid polymerase in a polymerization reaction, and the Y's represent multiple copies of a detectable molecule.

Another aspect of the present invention provides a Simtide useful in sequencing, labeling or probing reactions having the structure:

wherein X is a nucleotide base, base analog, or any other base mimic which may be incorporated by a nucleic polymerase in a polymerization reaction, and D, Y and Z are different detectable molecules.

Alternatively, another aspect of the present invention provides a compound useful in sequencing, labeling or probing reactions having any of the structures indicated above, wherein the linker is a thio group instead of PBA.

Partial or complete Simtides can be introduced into oligonucleotides or polynucleotides during any standard or modified sequencing reaction, by chemical synthesis or by the use of nucleic acid enzymes, such as by one or more polymerases. The use of DNA polymerases to incorporate the above-mentioned Simtides of the present invention into oligonucleotides or polynucleotides is particularly preferred.

Although in principal all compounds encompassed within the structural formulas described herein may be prepared and used in accordance with the present invention, certain of the compounds are more readily prepared or used or both, and are, therefore, preferred.

Y may be any molecule capable of forming a detectable complex with a polypeptide when the modified nucleotide is incorporated into a nucleic acid containing either deoxyribonucleic or ribonucleic acids, or analogs or mimics thereof. Y may, therefore, be any ligand, which possesses these properties, including haptens which are only immunogenic when attached to a suitable carrier but are capable of interacting with appropriate antibodies to produce complexes. Biotin and iminobiotin are preferred Y molecules.

More than one type of or mixtures of reversible linkers and/or detector molecules may be used. These linkers/detector molecules can be attached to more than one attachment site in a sequencing fragment. Linkers can be coupled via functional groups to one or more different sites on the detectable molecules, or attached to more than one detectable molecule. Detectable molecules may also be linked to more than one base in a sequencing fragment.

In a preferred embodiment of the present invention, X is selected from the group consisting of purines and pyrimidines. Pyrimidine bases include cytosine, uracil and thymine. Purine bases include guanine and adenine. The sugar of the nucleotide component of the Simtide of the present invention can be ribosome or deoxyribose.

It is recognized that novel or unique bases or base analogs not included in the four normal bases can be employed in the present invention. Such novel or unique bases or base analogs can include, but are not limited to, bases, base analogs or "mimics" such as difluorotoluene deoxynucleosides (Rawls, R., 1997), or other molecules which can be incorporated by a nucleic acid polymerase.

Modified nucleotide molecules, such as pseudouridine or other molecules which can be utilized to generate polymers similar to nucleic acid but which are more stable than nucleic acids (e.g., PNA monomers), may be utilized in the sequencing reactions employed in connection with the present invention.

The modified nucleotides according to the present invention preferably contain a nucleotide base associated with a reversible linker arm, which in turn may be associated with a detectable molecule. The reversible linker arm can be associated at various positions of the bases. For example, linkers can be associated at 3', 5', or 7' positions on bases, or 2' or 3' positions on sugars. Examples for synthesizing nucleotides associated with reversible linkers, particularly linkers mentioned above, are provided herein.

Moreover, methods of attaching chemical moieties to pyrimidine and purine rings are known. A simple and rapid acetoxymercuration reaction is known for introducing covalently-bound mercury atoms into the 5-position of the pyrimidine ring, the C-8 position of the purine ring or the C-7 position of a 7-deazapurine ring, both in nucleotides and polynucleotides. (R. M. K. Dale, et al., *Proc. Natl. Acad. Sci. USA* 70, 2238 (1973); R. M. K. Dale, et al., *Biochemistry* 14, 2447, (1975)). It has also been shown that organomercurial compounds react with olefinic compounds in the presence of palladium catalysts to form carbon-carbon bonds (R. F. Heck, *J. Am. Chem. Soc.* 90, 5526 (1968)). Recently, this reaction scheme has been applied in the synthesis of C-5 substituted pyrimidine nucleotide compounds (C. F. Bigge, et al., *J. Am Chem. Soc.* 102, 2033 (1980).

It is a specific object of the present invention to provide a nucleotide base in which a reporter group is attached via a reversible linker arm to the nucleotide, said nucleotide base being useful in sequencing, labeling or probing reactions.

In the present invention, the linkage generated via the linker arm is preferably reversible. The length of the linker arm can be adjusted according to the application. When reversible linkers according to the present invention are utilized, the versatile nucleotides are generated for sequencing or probing reactions. Pre-linked nucleotides (unmodified, or modified with part or all of the reversible linker) can be incorporated into a sequencing reaction, and the linkage can be completed after the reaction, to yield a detectable fragment. Alternatively, if incorporatable by nucleic acid enzymes, such as polymerases, linked nucleotides can be utilized directly, incorporated into the reaction, and molecules detected according to standard techniques. Nucleotides associated with linker molecules can be incorporated into sequencing fragments. Simtides can then be generated on treatment of the fragments with detector molecules derivatized to contain thiols.

It is recognized that any linkage group or groups can be attached at various positions of a nucleotide. The general synthetic approach adopted for associating the linker or linker parts to bases and detectable molecules is described herein. Parts of the linker may be attached to the base(s) and the detectable molecule(s), followed by association of the linker parts, or a complete linker may be first attached to the base(s) and the detectable molecule(s) followed by attachment to the other component.

Linker molecules of the present invention are molecules that in certain preferred embodiments allow reversible connection or association of the bases or base analogs to detector molecules. Typically, the linkers contain one or more reactive groups, allowing the linkers to associate and preferentially to be cleaved or disconnected by means or a specific reaction or reaction steps. Linkers also have appropriate functional groups at each end for coupling to the bases and to the detector molecules. Particularly preferred linkers are those whose cleavage, disconnection, or disassociation is reversible and controllable. Illustrative examples of suitable linkers include bioconjugates such as Phenylboronic Acid (PBA), DNA binding proteins, and disulfide-based coupling systems.

Cleavable linkers may also consist of a cleavable component and a constant component, which is the same for either all bases or for all detector molecules. The constant part may comprise chemical compounds which permit attachment to both the cleavable part of the linker and to other chemical groups or other molecules. An example of a constant component is an invariable part of a detector molecule.

There are a variety of linkers that may be useful in the present invention. For instance, linker molecules may be based upon the phenylboronic acid complexing moieties (Yurkevich, 1969). Phenylboronic acids are known to interact with a wide range of polar molecules having the requisite functionalities (Middle, 1983; Frantzen, 1995). Phenylboronic acid, like boric acid, is a Lewis acid and ionizes not by direct deprotonation but by hydration to yield the tetrahedral phenylboronate anion (pKa-8.86). A variety of phenylboronic acid molecules with varying pKa's are commercially available. Molecular variations can also be generated. Ionization is fundamental for complexation causing a change from trigonal coordination to tetrahedral coordination. Bioconjugation with phenylboronic acid molecules has been achieved between compounds having diol functionalities (e.g. carbohydrates) to immobilized phenylboronate anion to form cyclic esters under alkaline conditions; release is effected by pH shifts. Phenylboronic acid-modified dUTP linker molecules have also been incorporated into oligomers using DNA polymerases as an alternative to DNA labeling and purification via biotin incorporation. Bioconjugation via linkers such as the phenylboronic acid linker can simplify the reversibility of the coupling reaction, enabling attachment of agent groups that cannot generally be incorporated by DNA polymerases. In addition, the phenylboronic acid molecule causes minimal interference with respect to DNA hybridization and base incorporation with a deoxynucleotide triphosphate attached to it.

Figure 1:
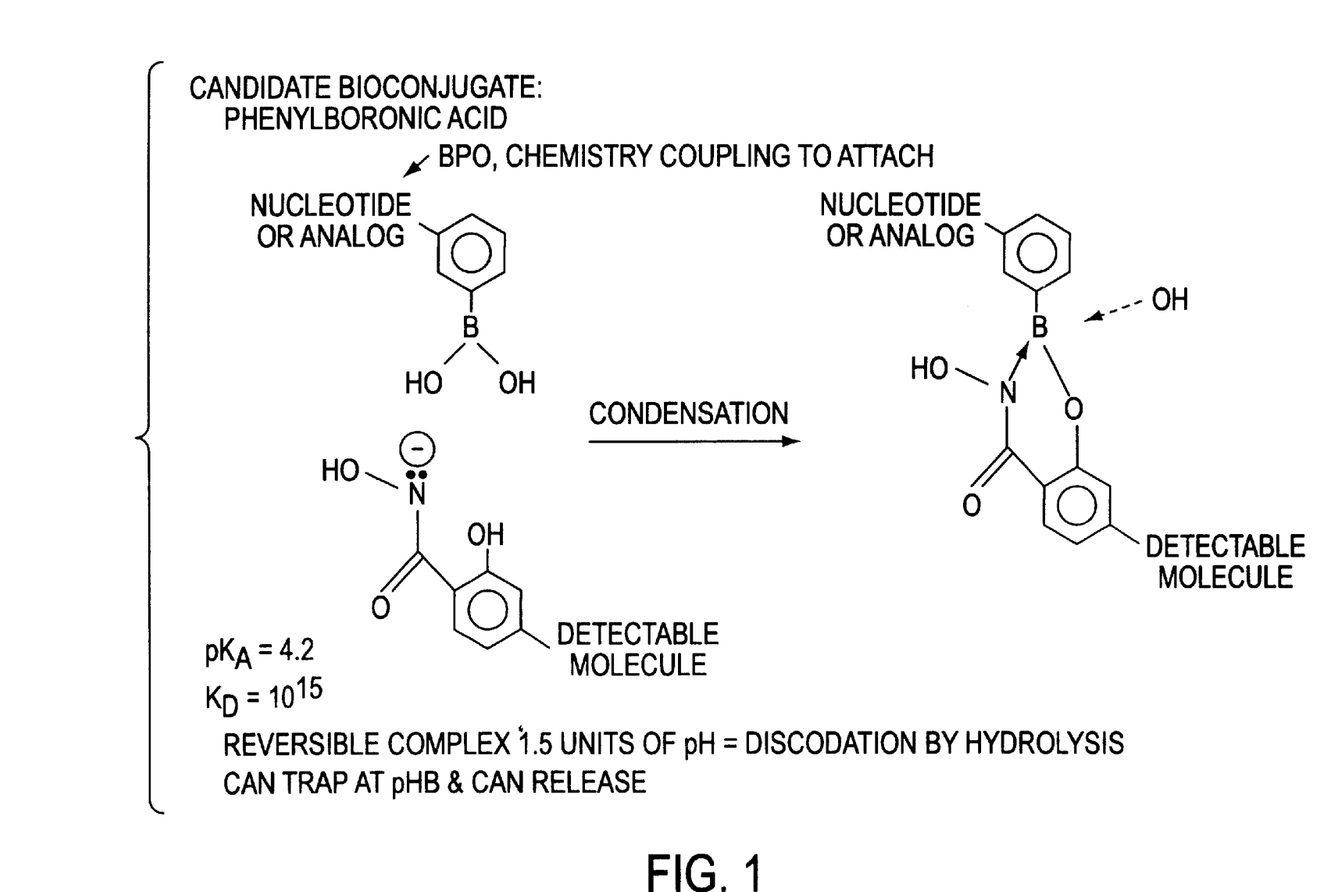
FIG. 1 depicts the use of phenyl boronic acid (PBA) as a reversible linker in the present invention.

Phenylboronic acid bioconjugate complexes are preferred for use as linker molecules in the present invention. Methods for associating and dissociating suitable linkers to many different types of potential molecules, such as to bases, are known to one of ordinary skill in the art. These methods include but are not limited to those described in WO 95/20591, as well as to those using biotin-streptavidin. FIG. 1 depicts this type of candidate bioconjugate, indicating the fact that standard chemistry can be used to attach one component of the bioconjugate (linker) to candidate nucleic acid bases, and to attach another component of the linker to candidate detector molecules. A condensation reaction then associates the linker components, creating a complex, or Simtide.

Figure 2:
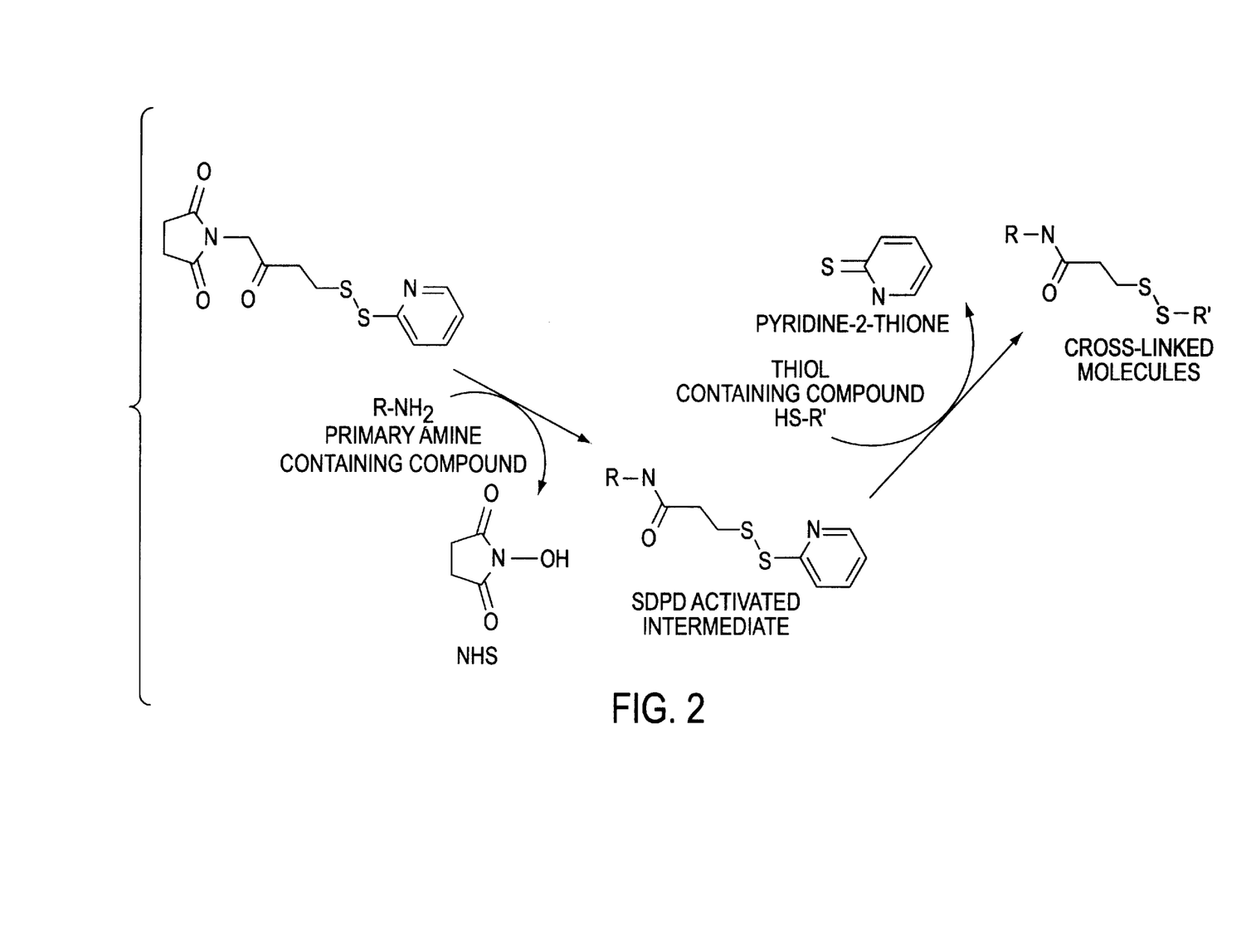
FIG. 2 depicts nucleoside triphosphate (NTP) linked by an amine-containing linker attached to the nucleoside base component of a Simtide; a detectable molecule may additionally be linked by a thiol-containing linker arm.

Disulfide-based coupling systems can also be utilized as linkers in the method of the present invention. Disulfide-based coupling systems, such as that described herein, offer the benefit of being reversible under mild redox conditions. The system is selective for thiol groups and nucleic acid is stable under the conditions in which the system functions. FIG. 2 depicts the nucleoside triphosphate linked by an amine-containing linker arm attached to the nucleoside base component of a Simtide. A detectable molecule can then be linked by a thiol-containing linker arm. This reversible linker system is useful in the present invention.

In the system depicted below, the nucleoside triphosphate can be linked by an amine-containing linker arm attached to the nucleoside base component. A detector molecule can then be linked by a thiol-containing linker arm.

Heterobifunctional cross-linkers, such as N-succinimidyl 3-[pyridyldithio]propionate (SPDP) (described by Hermanson, Greg T., Bioconjugate Techniques, Academic, San Diego, Calif. 1995, p.230, available from Pierce), which link amino-containing molecules to a thiol-containing molecule can be employed. The heterobifunctional cross-linker SPDP is available from Pierce as are other related crosslinkers with different chain lengths, making this a versatile system for manipulation of the distance between the nucleic acid base and the detector molecule of interest. The 5-position of cytidine and uridine, and the 8-position of adenine and guanine are preferable positions for association in a disulfide-based coupling system.

Alternatively, a diazirine coupling system may be used to incorporate the linker into a modified nucleotide containing a thiol group through the maleimide portion and the chemical group (CG) through the aryldiaziridine portion.

Thus, the present invention provides a novel molecule termed a Simtide for use in any sequencing method. Detectable molecules are associated via linkers to nucleic acid bases or base analogs on any variety of positions. In one aspect of the present invention, dideoxynucleotides are coupled to one or more detectable molecules in the sequencing reaction to generate end-labeled fragments. In another aspect, a single nucleotide is attached to a linker or linker component, the sequencing reaction is performed, and the detectable molecule or molecules is attached last. In still another aspect of the present invention, different detectable molecules are associated with dideoxynucleotides or nucleotides to allow sequencing to occur in a single, combined reaction lane in a sequencing gel or a single tube in an automated sequencer. Multiple detectable molecules can be attached to single bases to be utilized in sequencing reactions.

In the method of the present invention, a series of novel nucleotide derivatives that contain detectable molecules associated with the ring structures of nucleotides are generated and utilized in sequencing or other reactions where labeling of nucleotide molecules is required or useful. These nucleotide derivatives, as well as polynucleotides and coenzymes that contain them, can interact with proteins such as avidin or antibodies. The interaction between modified nucleotides and specific proteins can be utilized as an alternative to radioisotopes for the detection of nucleic acid components in sequencing reactions.

Detectable molecules, such as fluorescent molecules or molecules linked to fluorescent dyes, can be linked to the nucleotide/linker components after the sequencing reaction to allow detection of the nucleic acid fragment. It is also contemplated that Simtides may be incorporated into an extending chain with acceptable efficiencies, thus having utility in sequencing reactions.

In a preferred embodiment of the present invention, Y is selected from the group consisting of infrared dyes, fluorescent dyes, luminescent molecules, colorimetric molecules, radioactive labels, molecules attached to any one of these dyes, proteins such as enzymes, heterobifunctional groups, and labels.

In the present invention, multiple detectable molecules may be attached to the base or base analog via reversible linkers. In particular, it is recognized that, for example, when sequencing is difficult, such as the sequencing of genomic DNA, multiple detectable groups associated with a nucleotide could provide higher sensitivity in the detection of the entire molecule generated via the sequencing reaction, allowing one to effectively utilize fewer template molecules in the sequencing reaction.

Multiple Simtides can also be utilized in the sequencing process to yield sequence information for any nucleic acid. For example, different nucleotide or nucleotide analogs may be linked to different detector molecules and utilized in sequencing reactions.

The reporter group is a chemical group which has a physical or chemical characteristic which can be measured or detected by appropriate detector systems or procedures. Examples of reporter groups can be found in U.S. Pat. Nos. 4,948,882 and 4,711,955, the disclosures of which are incorporated herein by reference. Detectability can be provided by evaluation of such characteristics as color change, luminescence, fluorescence or radioactivity, or it can be provided by the ability of the reporter group to serve as a ligand-recognition site. Such characteristics can be measured or detected, for example, by the use of conventional colorimetric, spectrophotometric, fluorometric or radioactivity-sensing instruments, or by visual inspection.

The interactions which can be usefully initiated by the reporter group defined herein include appropriately specific and selective interactions productive of groups or complexes which are themselves readily detectable, for example, by calorimetric, spectrophotometric, fluorometric, or radioactive detection procedures. Such interactions can take the form of protein-ligand, enzyme-substrate, antibody-antigen, carbohydrate-lectin, protein-cofactor, protein-effector, nucleic acid-nucleic acid and nucleic acid-ligand interactions. Examples of such ligand-ligand interactions include fluorescein-anti-fluorescein antibody, dinitrophenyl-dinitrophenyl antibody, biotin-avidin, oligonucleotide-complementary oligonucleotide, DNA-DNA, RNA-DNA and NADH-dehydrogenase. Either of each such ligand pair may serve as a ligand recognition type reporter group. Preferred reporter groups of the present invention include biotin, fluorescein, digoxigenin, phenyloxazolone, tetramethyl rhodamine, Texas Red and BODIPY.

Many procedures employed in recombinant DNA technology rely heavily on the use of nucleotide or polynucleotide derivatives radioactively labeled with isotopes of hydrogen ($^3$H), phosphorus ($^{32}$P), carbon ($^{14}$C), or iodine ($^{125}$I). Such radioactive compounds provide useful indicator probes to detect, monitor, localize, or isolate nucleic acids and other molecules of scientific or clinical interest and other molecules of scientific or clinical interest, even when present in only extremely small amounts. To date, radioactive materials have provided the most sensitive, and in many cases, the only means to perform many important experimental or analytical tests.

It is known that haptens can combine with antibodies, but can initiate an immune response only if bound to a carrier. This property can be exploited in detection and identification testing. It is also known that biotin and iminobiotin strongly interact with avidin, a 68,000 dalton glycoprotein from egg white. This interaction exhibits one of the tightest, non-covalent binding constants (Kdis=10–15) seen in nature. If avidin is coupled to potentially demonstrable indicator molecules, including fluorescent dyes, e.g. fluorescein or rhodamine; electron-dense reagents, e.g. ferritin, hemocyanin, or colloidal gold; or enzymes capable of depositing insoluble reaction products, e.g. peroxidase or alkaline phosphatase, the presence, location, or quantity of a biotin probe can be established.

As used herein, a detector molecule is any molecule which is to be attached to a base by the linker.

General methods for joining the linker arm and reporter group to the nucleotides are known to those skilled in the art and examples are provided herein.

These and other aspects of the present invention will be apparent to those skilled in the art. This invention will be better understood from the Examples which follow. However, one skilled in the art will readily appreciate that the specific methods and results discussed herein are merely illustrative of the invention, which is defined by the claims that follow thereafter.

EXAMPLES

Example 1

Generation of Simtides

The following Example describes one method to generate a Simtide to be utilized in a sequencing reaction.

Modification of nucleotide to accept label:

1. Mercuration of the nucleotide:
dUMP+Hg(OAc)$_2$→5-Hg-dUMP
Conditions: 0.1M NaOAc buffer, pH 6

1. Conversion of the mercurated nucleotide to the 5'-allylamine derivative
   5-Hg-dUMP+CH$_2$=CHCH$_2$NH$_3$→5'-allylamine-dUMP
   Conditions: 0.1M NaOAc buffer, pH 5

2. Protection of the amine and activation of the 5'-phosphate
   5'-allylamine-dUMP+TFA anhydride→dUMP-5'-TFA amide, 5'-TFA-phosphate mixed anhydride 3. Conversion to the triphosphate using tributylammonium pyrophosphate (TBAPP)
   5'-TFAA, 5'-TFA-dUMP+TBAPP→dUMP-5'-TFAA dUTP
   Conditions: 0.1M N-methylimidazole 4. The amide is then deprotected in ammonium hydroxide to yield the final 5'-allylamine dUTP.

The final material is purified by chromatography on DEAE-cellulose and reverse-phase HPLC (RP-HPLC) using standard protocols.

The same steps can be used to make ddUTP and the corresponding allylamine derivative using ddUMP as the starting material.

5. The allylamine derivatives are converted to the sulfhydryl reactive form using SPDP in 10-fold molar excess, then repurified by RP-HPLC.

6. Conversion to the Triphosphate using Tributylammonium Pyrophosphate-(TBAPP)

5-allylamine-dUTP+SPDP dUTP→5'-SPDP dUTP
Conditions pH 7–9

The following represents a general synthesis method for nucleotide tiphosphates useful in the present invention:

The first step is mercuration. Alternatives include iodination with similar steps following.

Trifluoroacetic anhydride

5-Propargylamine dideoxy-UTP

5-SPDP dideoxy-UTP

Final modification with fluorescent dye:

The following depicts a general method for modification of an near-infrared fluorescent dye (IR-780) and association with an amine-terminated DNA fragment to yield a Simtide useful in a sequencing reaction according to the present invention:

IR-780

IR-780 N-hydroxysuccinimide ester

Alternative methods for modification of nucleotides are depicted in the following:

Deprotection/Exchange

A. S-acetylthioester (e.g. 3'SATA 3'thio ddUTP):

B. SPDP (e.g. 5'-SPDP-dUTP or ddUTP or ddUTP or dNTP):

A.1. reduction:

RSH = mercaptoethanol dithiothreitol

B.1. disulfide exchange:

C. Amine Trifluoroaceide (eg. 3'-TFA anide ddUTP):

Derivatization with Various Fluorophores is depicted in the following:

A.

Fluorescein isothiocyanate thiourea

B.

X = Cl, I or Br
e.g. Chloromethyl fluorescein

Fluorescein maleimide

Thioether derivative

Example 2

Another specific application uses 3'amino didoxynucleotide triphosphates (partial Simtides) in the sequencing reaction, followed by coupling with amino-reactive fluorescent dyes to generate complete Simtides prior to detection using an automated DNA sequencer.

This procedure involves the following steps:
1. The synthesis and purification of all four 3'-amino ddNTPs.
2. Incorporation of the modified ddNTPs in a sequencing reaction using thermostable DNA polymerases.
3. Post-incorporation derivatization to four different amine-reactive fluorescent dyes.

These steps are described below.

1. Synthesis & Purification of 3'-Amino Dideoxynucleoside Triphosphates

Base amine protected 3'-amino-dideoxy nucleosides are obtained commercially (e.g., RI Chemical (Orange, Calif.) or Monomer Sciences (Huntsville, Ala.)). The base exocyclic amines are protected to prevent reaction with phosphorus oxychloride in the conversion to the monophosphates. The 3'-amine is derivatized to the non-reactive trifluoroacetamide. The protected nucleosides are then reacted with $POCl_3$ in tri-alkylphosphine which allows selective reaction with the 5'-hydroxyl. Typically, reaction to the monophosphate is complete in less than one hour and is nearly quantitative. The remaining chloride is hydrolyzed with pyridine:water (1:10) and the intermediate purified on DEAE Sephadex. The monophosphate is dried, dissolved in arhydrous pyridine and reacted with pyrophosphoryl chloride to yield the triphosphate. The remaining chlorophosphates are again hydrolyzed in pyridine:water and purified. Further purification of the products of each of the above reactions is achieved using HPLC on Dionex Nucleopak eluting 0–0.5M NaCl in 20 mM Tris (pH 8) over 40 minutes. Elution is followed spectrophotometrically and factions collected accordingly. Spectra of the major products are correlated with NMR and mass spectrometry to conform identity. The resulting products are stored dry under argon at –20° C.

2. Incorporation of the ddNTP in a Sequencing Reaction

The incorporation of 3'amino ddNTh as a chain terminator is performed in a manner similar to a standard sequencing reaction, except that buffer systems without amine groups to facilitate dye labeling are introduced at this point.

Typically, 0.45 mM of each dNTP and 0.045 mM of the modified ddNTP will be used in the termination mix. The elongation reaction will be performed using 0.5 nmol DNA template, 2 pmol primer, 5 units of thermostable DNA polymerase, in 20 mM Bicine/NaOH, 2.5 mM $Mg^{2+}$ buffer. The elongation reaction is performed in a thermocycler using 30 cycles of 95° C. for 30 seconds, 50° C. for 15 seconds, and 70° C. for 60 seconds.

3. Dye Labeling of Sequencing Fragments

Amine modification reactions using isothicyonates and N-hydroxy succinimide esters have been well documented (G. T. Hermanson (1996), *Bioconjugate Techniques*, Academic Press) and nearly all dye isothiocyanates and NHS derivatives behave similarly.

Fluorescein Isothiocyanate (FITC) is made to 10 mg/ml in dry DMSO or DMF and the DNA fragments with free 3'-amine are dissolved in 1 ml 0.1 M sodium bicarbonate. FITC is added dropwise with siring and after one hour the reaction is purified over G-25 spun columns. The extent of derivatization of dye-labeled DNA fragment oligonucleotides will be determined spectrofluorometrically using the known molar extinction coefficients for DNA and fluorophores. DNA conjugated to dye or fluorophore is required at a final $A_{260}$ of about 1. The concentration of the dye is based on the molar extinction of the dye.

What is claimed is:

1. A method for determining the nucleotide sequence of a target nucleic acid, the method comprising:

a) generating labeled nucleic acid fragments which are complementary to a selected target nucleic acid molecule;

b) incorporating into the nucleic acid fragments by a nucleic acid polymerase, a complex comprising a detectable label molecule, a reversible linker, and a nucleotide base or analog thereof;

c) separating the labeled fragments by size separation; and d) detecting the labeled molecule, wherein the reversible linker is phenylboronic acid or a derivative thereof.

2. The method of claim 1 wherein the complex is incorporated into the nucleic acid fragments as a primer.

3. The method of claim 1 wherein the complex is incorporated into the nucleic acid fragments as a chain elongator.

4. The method of claim 1 wherein the complex is incorporated into the nucleic acid fragments as a chain terminator.

5. The method of claim 4 wherein the nucleotide base is a dideoxynucleotide.

6. The method of claim 1 wherein the complex comprises two or more label molecules.

7. The method of claim 1 wherein the label molecule is selected from the group consisting of fluorescent labels, chemiluminescent labels, colorimetric labels, radioactive labels and infrared labels.

8. The method of claim 1 wherein the complex is incorporated into the nucleic acid fragments as a complete complex.

9. The method of claim 1 wherein the complex is sequentially incorporated by first incorporating a partial complex into the nucleic acid and subsequently associating with the partial complex the label molecule prior to detecting the label molecule.

* * * * *